United States Patent [19]
Weitz, Jr.

[11] Patent Number: 4,965,731
[45] Date of Patent: Oct. 23, 1990

[54] SYSTEM AND METHOD OF SPECIFIC FLIGHT JET AIRCRAFT OPERATION

[75] Inventor: Paul G. Weitz, Jr., Cornwall, Vt.

[73] Assignee: Simmonds Precision Products, Inc., Wilmington, Del.

[21] Appl. No.: 247,480

[22] Filed: Sep. 22, 1988

Related U.S. Application Data

[63] Continuation-in-part of Ser. No. 901,096, Aug. 27, 1986, abandoned.

[51] Int. Cl.$^5$ .............................................. G01N 25/30
[52] U.S. Cl. ..................................... 364/442; 374/143
[58] Field of Search ...................... 364/442, 557, 558; 431/12; 73/32 R, 861.01; 374/36, 142, 143

[56] References Cited

U.S. PATENT DOCUMENTS

| | | | |
|---|---|---|---|
| 3,285,320 | 11/1966 | Clark | 431/12 |
| 4,345,463 | 8/1982 | Wilson et al. | 374/36 |
| 4,384,792 | 5/1983 | Sommers et al. | 374/36 |
| 4,809,174 | 2/1989 | Momenthy | 364/442 |

*Primary Examiner*—Gary Chin
*Attorney, Agent, or Firm*—Dale R. Lovercheck

[57] ABSTRACT

A system and method of operation of a jet aircraft for a specific flight. The mass of liquid fuel in the aircraft's fuel tank is determined from the actual heating value of the fuel, based upon its density and temperature. The flight time available from the amount of fuel in the tank is determined and displayed. At least the amount of the fuel required for a specific flight is loaded into one or more fuel tanks on the aircraft.

13 Claims, 5 Drawing Sheets

SYSTEM AND METHOD OF SPECIFIC FLIGHT JET AIRCRAFT OPERATION

This is a continuation-in-part of U.S. patent application Ser. No. 901,096 filed Aug. 27, 1986.

BACKGROUND OF THE INVENTION

The invention relates to a system and method of determining preciously the heating value of liquid jet a fuel and the amount of flight time which will be provided by an amount of that fuel. More particularly, the invention provides a system and a method of determining the amount of the net heating value and of flight time (at conditions of flight) which will be provided by an amount of liquid jet fuel to within ±0.4%. The prior art does not provide a method or system which determines the net heating value and flight time provided by an amount of fuel to within ±0.4%.

Dougherty, et al., in U.S. Pat. No. 4,258,422, discloses the use of fuel density sensors in a liquid gauging system. A system read out is provided for fuel quantity in weight, such as pounds, using a measurement of fuel density. The fuel density may be used with fuel volume to compute fuel weight. In order to determine fuel density, the dielectric constant of the fuel may be measured by a fuel density sensor. In conjunction with the analogue circuitry within the primary indicator, a system microcomputer may then compute a fuel density value using a relationship between dielectric constant and density. One density sensor is installed in each fuel tank such that the density sensor is completely covered by fuel when the system is in operation. I. H. Cohn, et al., in U.S. Pat. No. 3,523,186, discloses an attitude error correction fluid gauging system employing radiation detectors and error storage techniques. An indicated volume signal is derived from the radiation detectors and a densitometer. Rosie, et al., in U.S. Pat. No. 4,229,798, discloses a liquid storage tank contents gauge which measures temperature by a sensor, such as a thermoster, a thermocouple or a resistance thermometer and the electrical signal produced controls a voltage controlled oscillator. Weitz, Jr., et al., in U.S. Pat. No. 4,011,746, discloses a liquid density measurement system which includes a temperature sensor and a capacitance probe. Stansfeld, U.S. Pat. No. 4,007,627, discloses a density transistor. Messer, U.S. Pat. No. 3,222,927, discloses a continuous process for determining moisture content and heat of combustion of solid fuels. Hartford, et al., U.S. Pat. No. 4,252,097, discloses a viscosity compensated fuel injection system. Swoboda, U.S. Pat. No. 4,442,700, discloses an ultrasonic hydrometer. Stansfeld, in U.S. Pat. Nos. 4,262,532 and 3,916,672, discloses the measurement of fluid density and specific gravity.

SUMMARY OF THE INVENTION

A system and method of operation of a jet aircraft for a specific flight. The mass of liquid fuel in the aircraft's fuel tank is determined from the actual heating value of the fuel, based upon its density and temperature. The flight time available from the amount of fuel in the tank is determined and displayed. At least the amount of the fuel required for a specific flight is loaded into one or more fuel tanks on the aircraft.

DETAILED DESCRIPTION OF THE INVENTION

Figure 1:
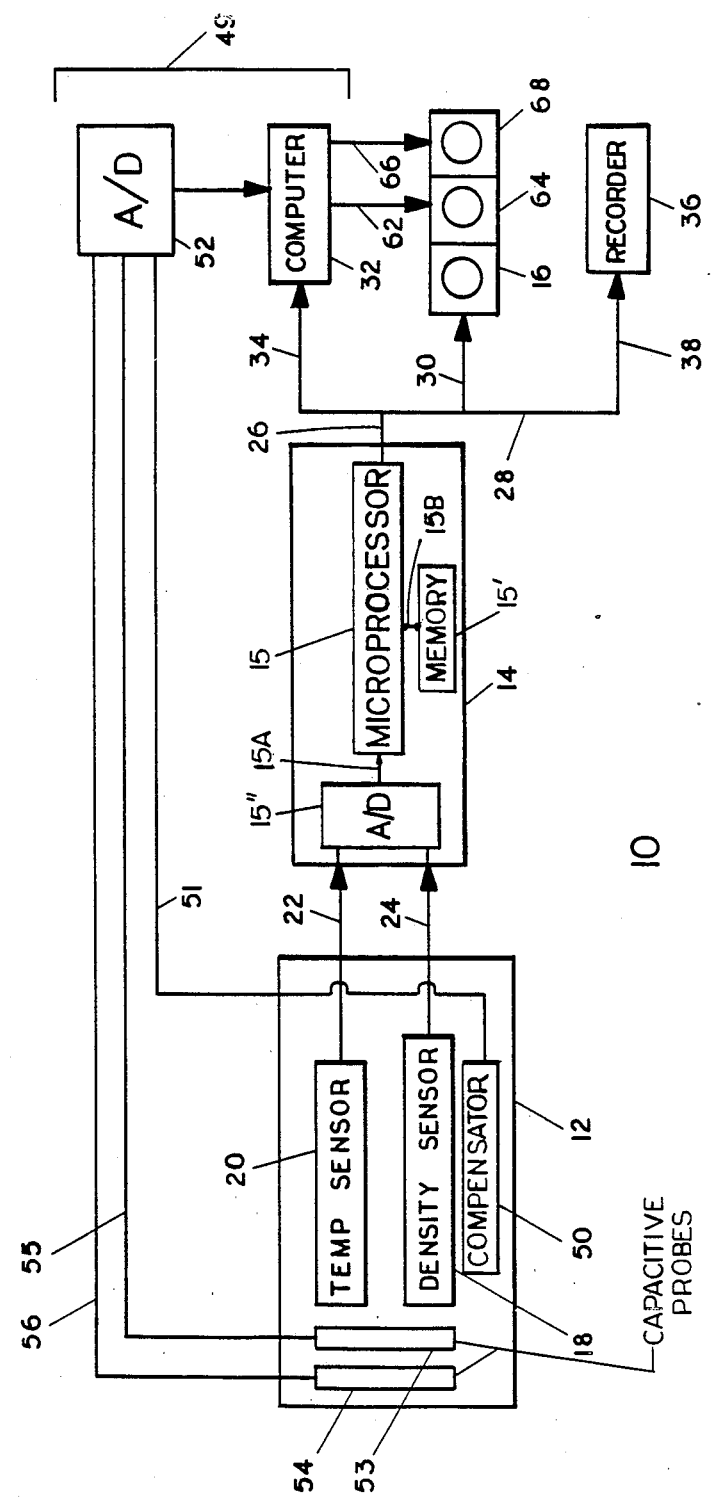
FIG. 1 is a schematic representation of a system for determining and displaying fuel heating value in accordance with the present invention.

The system and method of the invention is now described with more particular reference to FIGS. 1-4. FIG. 1 shows a system for determining and displaying fuel heating value is shown generally at 10. The system 10 includes fuel container 12, signal conditioner 14, and display 16. The signal conditioner 14 includes microprocessor 15, memory 15' and analog to digital converter (A/D) 15''. The density sensor 18 and the temperature sensor 20 are supported by fuel container 12.

The signal conditioner 14 receives temperature and density signals through lines 22 and 24 respectively from temperature sensor 20 and density sensor 18. Signal conditioner 14 converts the density signal to a heating value signal. The display 16 receives the heating value signal from signal conditioner 14 through lines 26, 28 and 30. The heating value signal is sent to computer 32 from line 28 through line 34. The heating value signal is sent to recorder 36 from line 28 through line 38.

The signal conditioner 14 stores information relating density to heating value at one or more temperatures for one or more fuel compositions. The information may be stored as data in a memory 15' for liquid jet fuels at a particular temperature listing the heating value and density of each fuel as shown in the Table below for fuels at 60° F.

TABLE

Density and Net Heating Value of Liquid Jet Fuels at 60° F.

| Density Pounds/Gallon | Net Heating Value BTU/Pound | Jet Fuel °API |
|---|---|---|
| 6.5909 | 18,662 | 47.3 |
| 6.6168 | 18,683 | 46.6 |
| 6.6617 | 18,638 | 45.4 |
| 6.6730 | 18,596 | 45.1 |
| 6.6996 | 18,573 | 44.4 |
| 6.7225 | 18,598 | 43.8 |
| 6.7263 | 18,614 | 43.7 |
| 6.7340 | 18,620 | 43.5 |
| 6.7340 | 18,589 | 43.5 |
| 6.7379 | 18,540 | 43.4 |
| 6.7456 | 18,627 | 43.2 |
| 6.7456 | 18,594 | 43.2 |
| 6.7456 | 18,608 | 43.2 |
| 6.7495 | 18,630 | 43.1 |
| 6.7533 | 18,577 | 43.0 |
| 6.7533 | 18,599 | 43.0 |
| 6.7533 | 18,603 | 43.3 |
| 6.7533 | 18,563 | 43.0 |
| 6.7533 | 18,612 | 43.0 |
| 6.7533 | 18,604 | 43.0 |
| 6.7611 | 18,556 | 42.8 |

TABLE-continued

Density and Net Heating Value of Liquid Jet Fuels at 60° F.

| Density Pounds/Gallon | Net Heating Value BTU/Pound | Jet Fuel °API |
|---|---|---|
| 6.7650 | 18,580 | 42.7 |
| 6.7650 | 18,594 | 42.7 |
| 6.7650 | 18,565 | 42.7 |
| 6.7650 | 18,585 | 42.7 |
| 6.7688 | 18,589 | 42.6 |
| 6.7727 | 18,566 | 42.5 |
| 6.7727 | 18,576 | 42.5 |
| 6.7727 | 18,591 | 42.5 |
| 6.7727 | 18,514 | 42.5 |
| 6.7727 | 18,594 | 42.5 |
| 6.7572 | 18,606 | 42.9 |
| 6.7805 | 18,597 | 42.3 |
| 6.7805 | 18,576 | 42.3 |
| 6.7922 | 18,590 | 42.0 |
| 6.7922 | 18,573 | 42.0 |
| 6.7922 | 18,565 | 42.0 |
| 6.7922 | 18,515 | 42.0 |
| 6.7962 | 18,536 | 41.9 |
| 6.7962 | 18,605 | 41.9 |
| 6.7962 | 18,583 | 41.9 |
| 6.8001 | 18,563 | 41.8 |
| 6.8001 | 18,520 | 41.8 |
| 6.8001 | 18,574 | 41.8 |
| 6.8040 | 18,562 | 41.7 |
| 6.8079 | 18,543 | 41.6 |
| 6.8119 | 18,515 | 41.5 |
| 6.8158 | 18,545 | 41.4 |
| 6.8158 | 18,544 | 41.4 |
| 6.8316 | 18,570 | 41.0 |
| 6.8316 | 18,542 | 41.0 |
| 6.8435 | 18,529 | 40.7 |
| 6.8515 | 18,544 | 40.5 |
| 6.8635 | 18,494 | 40.2 |
| 6.8635 | 18,528 | 40.2 |
| 6.9403 | 18,492 | 38.3 |
| 6.9731 | 18,457 | 37.5 |

The use of net heating value based upon energy per unit mass such as BTUs per pound is preferred as it is measured with less variation than net heating value based upon energy per unit volume. The jet fuel samples shown in the Table have net heating values of from 18,683 BTU/pound to 18,457 BTU/pound at 60° F. This shows a 1.2% (226 BTU/pound) variation in net heating value in BTU/pound. By measuring the density of a fuel sample the actual net heating value is more accurately determined with a 0.4% (70 BTU/pound) variation. Thus, by using net heating value based upon density BTU/pound the accuracy of net heating value is improved by 200 percent. This improved accuracy is beneficial in loading less fuel onto the aircraft for a given flight time and/or distance. The improved accuracy of net heating value provided in accordance with the invention correspondingly improves the accuracy of the flight time and distance available from the fuel remaining in an aircraft fuel tank during a flight.

Figure 2:
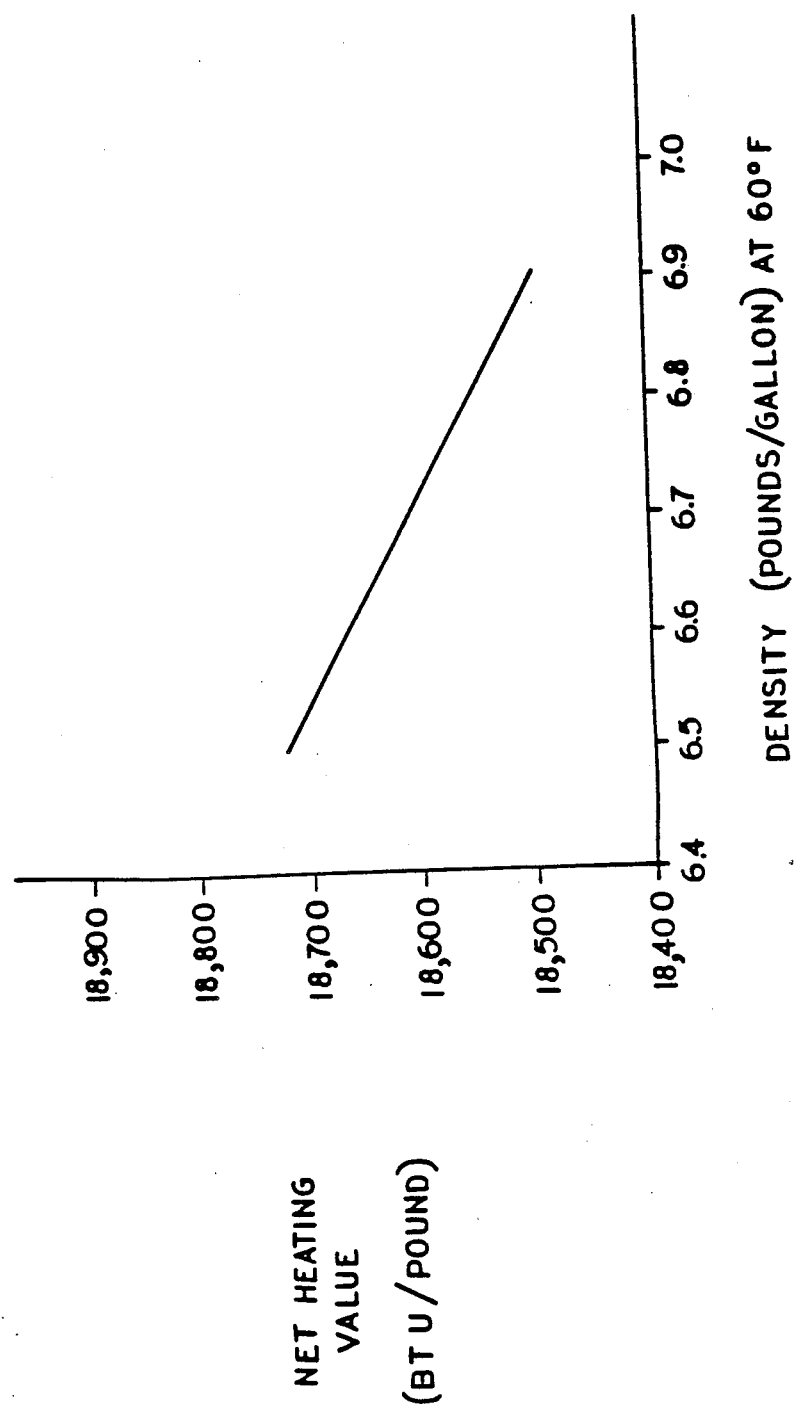
FIG. 2 shows the graphic relationship of density to net heating value for related jet fuel compositions.

Alternatively, the information relating density to heating value may be stored in the signal conditioner as an algorithm. While this alternative is less exact that the listing of heating values, it requires less storage of data. The relationship of density to net heating value may be treated as being linear (as shown in FIG. 2 for liquid jet fuels at 60° F.). Thus, net heating value N is equal to a constant C (571 BTU-gallon/pound$^2$) multiplied by density D (at 60°) as shown in equation I as follows:

$$N = CD \quad \text{(I)}$$

With more particular reference to FIG. 2 the graphic relationship of density to net heating value for a particular jet fuel composition at 60° F. is shown. This relationship is linear and may be stored as an algorithm or as data in the memory 15' of the signal conditioner. The net heating value of the fuel may be in units of BTU per pound. Alternatively, net heating value (also called heat of combustion) may be in units of BTU per gallon. The relationship of net heating value to density may be provided using the unitless density ratio of specific gravity in place of density.

A system and method for determining fuel heating value is provided using temperature and density signals. A signal conditioner transmits heating value signals. In the operation of jet aircraft the weight of fuel required to make a flight of a given period of time is determined by multiplying the flight time by the weight per hour of fuel required for the flight. The determination of heating value does not rely on lower heating value minimum which is usually less than the actual heating value. In a particular jet fuel for example, the lower heating value (minimum) may be 18,400 BTUs per pound while the actual heating value (net) is between 18,400 and 18,900 BTUs per pound. Thus, by accurately measuring the actual heating value to an accuracy within plus or minus 0.2%, it is possible to reduce the required fuel load for a specific flight by as much as 2.25%.

A list of density and net heating value (similar to the Table) is generated for typical temperatures expected during operation both on the ground and in flight. Each such list is stored in memory 15'. In operation the temperature of the fuel is measured using temperature sensor 2.0. The temperature is used to select which list (as shown in the Table for 60° F.) in which to search net heating value to find the density of the particular fuel in the aircraft fuel container 12. The density is measured using density sensor 18, and the density so measured is located in the list (in memory 15' for the temperature measured) to find the net heating value of the fuel in container 12.

Figure 4:
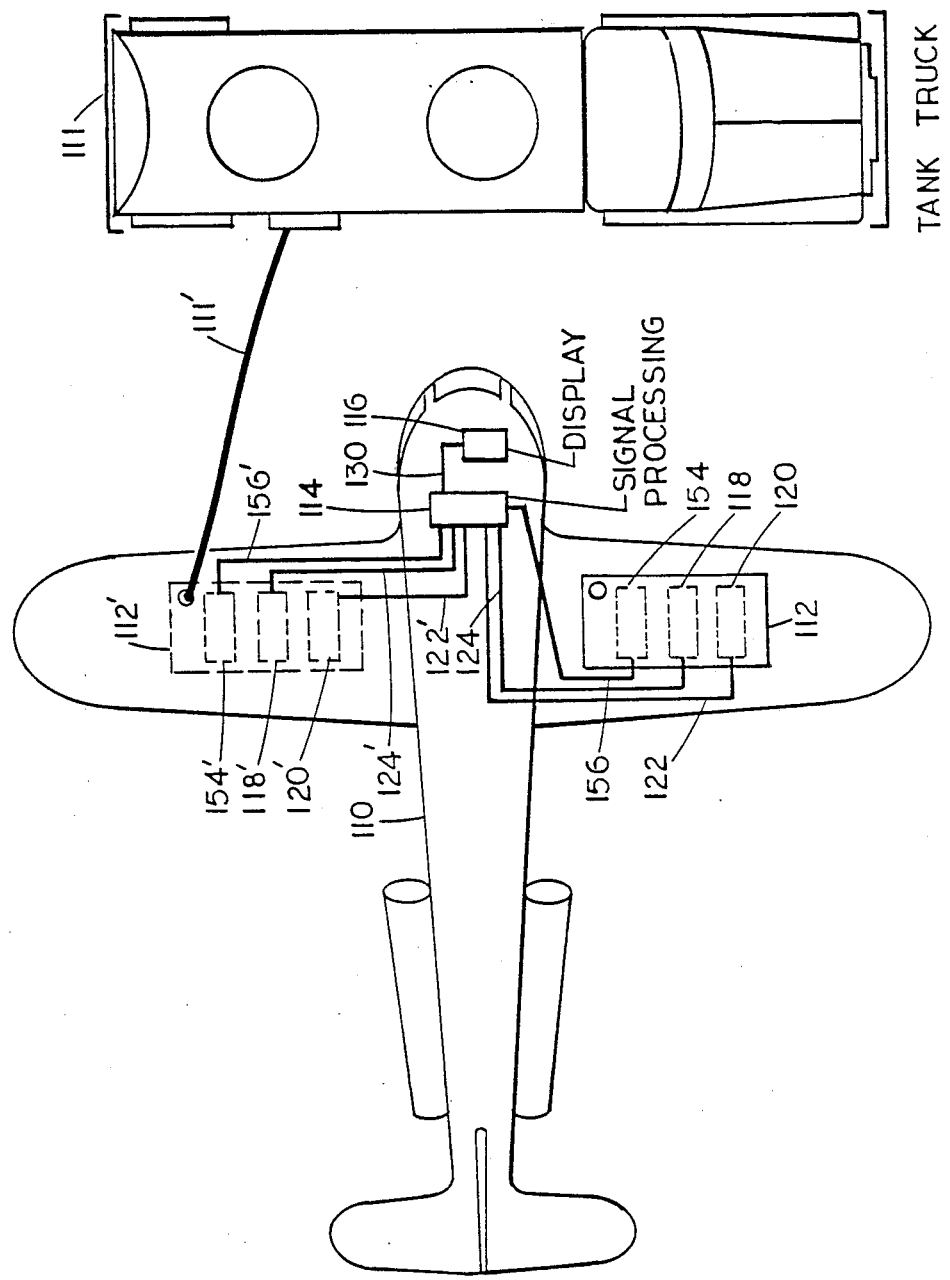
FIG. 4 shows an aircraft and mobile storage tank for use in determining, displaying and loading fuel onto the aircraft for a specific flight in accordance with the invention.

The gross heat of combustion is a function of specific gravity for all hydrocarbon fuels, but the net heat of combustion depends upon the hydrogen-carbon ratio; the difference between net and gross values are largest for the fuels containing the most hydrogen. On a weight basis, the fuels highest in hydrogen have the greatest heating value. Heat of combustion on a volume basis is related to specific gravity. On a volume basis, fuels which are lowest in hydrogen have the greatest heating value. The Gas Turbine Injury Handbook on page 180 at FIG. 4 shows the heat of combustion on a volume basis related to the specific gravity and aniline point. The relationship of heat of combustion in BTUs per gallon and specific gravity varies with temperature. For common liquid jet aircraft fuels, net heating value in BTUs per pound and density in pounds per gallon varies linearly at a particular temperature as shown in FIG. 2.

The fuel quantity Q (in pounds) required for an amount of flight time t (in hours) is related to the rate of fuel use R (in pounds per hour) during the flight as shown in equation II as follows:

$$Q = (R)(t) \quad \text{(II)}$$

Previously, in determining flight time available from an amount of fuel, the minimum heating value for the type of fuel would be used. The present invention improves the accuracy of such flight time determination by using the actual heating value of the fuel. The lower heating value (minimum) is less than the actual heating value. By accurately determining the actual heating value of the particular fuel to be combusted during the specific flight, the amount of fuel required for the specific flight and the flight time available from a specific amount of fuel, can be determined to an accuracy improved by at least 200%. The accuracy is given by the ratio of the difference between the actual heating value and the minimum heating value to the minimum heating value. The improvement in accuracy is equal to the percentage variation in heating value between lower heating value (minimum) and actual heat value for fuels of the same type. Typically, the variation in heat value between lower heating value (minimum) and actual heating value for liquid jet fuels of the same type is about 3% or less. Thus, up to 3% less fuel would need to be loaded and carried to make a specific flight by accurately determining the actual heat value of the specific fuel to be combusted during the flight. This reduction in fuel carried provides a savings in the amount of fuel consumed, because less weight is carried on the specific flight.

Solartron Aerospace Products provides an avionic liquid densitometer which is not influenced by secondary factors such as fuel type or source and is suitable for connection to most microprocessor based equipment. The densitometer comprises a sensor head, normally installed within the fuel tank, and mounting flange which also contains the conditioning electronics. A preferred avionic liquid densitometer includes a vibrating element.

The signal conditioner of the system of the present invention preferably includes a microprocessor in order to utilize memory containing fuel heating values for each of several fuels at several operating temperatures and to calculate the average value of the energy content of the fuel on board the aircraft.

The accuracy of the invention is determined by using two different fuels each with a significantly different heating value to fly an aircraft over a prescribed course while measuring the heating value with the system in accordance with the present invention. The aircraft is weighed before and after the flight to measure the fuel use. Samples of the fuel are tested for heating value in a laboratory as a check on the accuracy of the system in accordance with the present invention.

The system in accordance with the present invention requires a fuel container, a densitometer with modified electronics to supply outputs for fuel density in pounds per gallon, fuel heating value in BTUs per pound and fuel temperature. A display device is also provided to show information. A thermocouple with a readout is used to provide the temperature sensing and signal display for use in accordance with the present invention.

Operation

Figure 3:
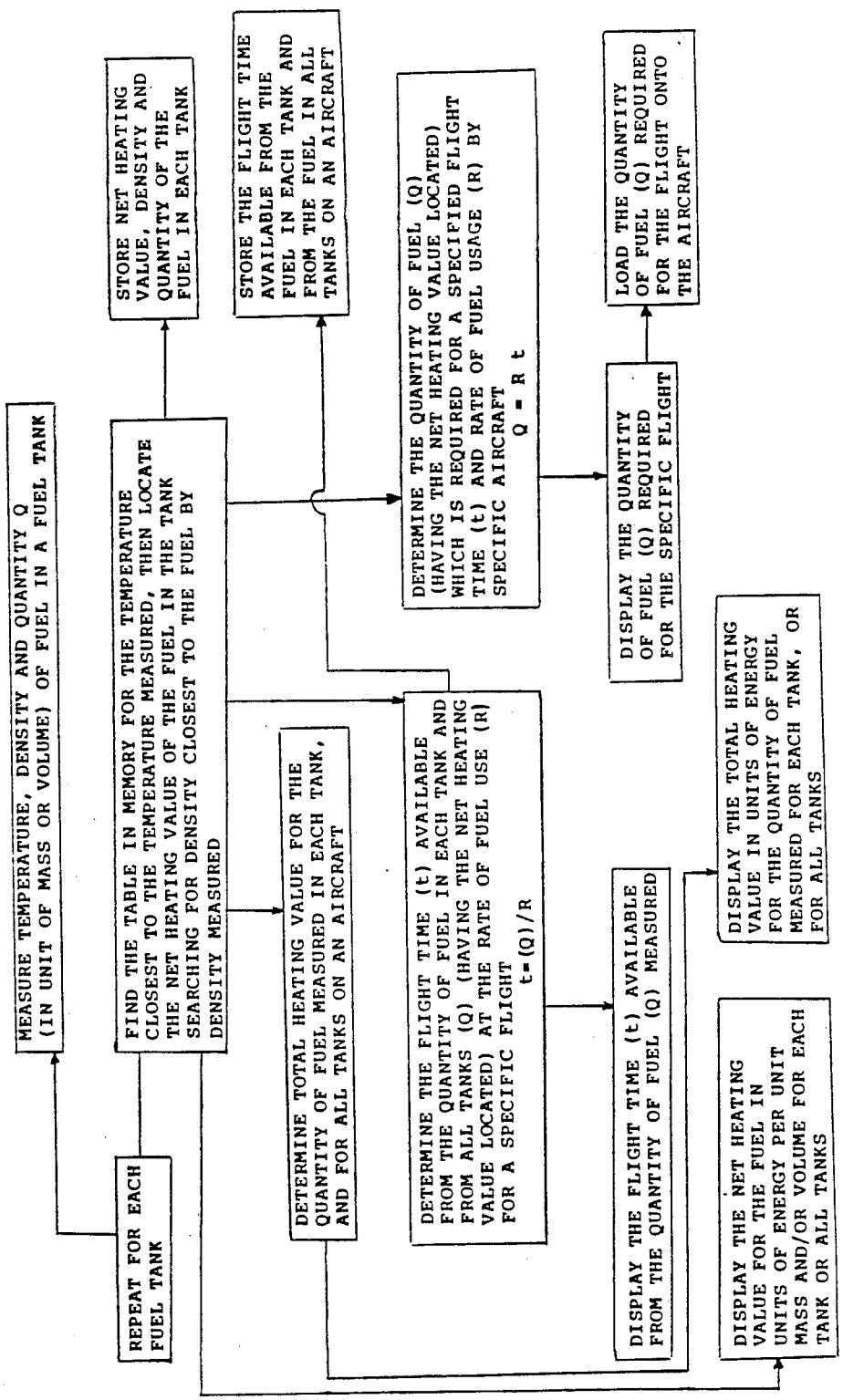
FIG. 3 shows the logical steps for determining and displaying net heating value, flight time available and fuel quantity required for a specific flight in accordance with the invention.

The heating value of the fuel in an aircraft fuel tank provides an indication of the energy per unit mass or volume available for combustion in the engines and thus ultimately the range of flight available for the aircraft at a given altitude and speed. As shown in FIG. 3 the present invention provides the pilot of an aircraft with an indication of heating value by first measuring the density and temperature of the fuel in the fuel tank and then converting the density and temperature measurements into a corresponding heating value. The conversion of density and temperature into the corresponding heating value may be carried out through the use of an algorithm which may be stored in software or a look-up table which may be stored in memory and accessed by a central processing unit. The heating value determined from the density and temperature by use of a stored algorithm or data related to heating value is then transmitted to a display indicator. The signal for heating value may simultaneously be conveyed to a central processing unit for the determination and subsequent display of flight time and/or flight distance based on heating value of the fuel and total fuel mass or volume. The total fuel mass or volume required for a specific flight time and/or distance for a particular type of aircraft operating with specific fuel heating value requirements per unit of time may also be determined and displayed.

A liquid gauging system 49 includes compensator 50 connected by line 51 to analog to digital electronics 52, (which corresponds to A/D electronics twenty-four of Dougherty, et al., U.S. Pat. No. 4,451,894, the disclosure of which is incorporated herein by reference in its entirety). Capacitive probes 53 and 54 are connected by lines 55 and 56 respectively to analog to digital electronics 52. Analog to digital electronics 52 is connected by line 60 to microcomputer 32. Microcomputer 32 is connected by line 62 to display 64. The liquid gauging system 49 determines the total fuel mass (or volume) which is multiplied by the heating value per unit mass (or volume) to provide the total heat content of the fuel on board the aircraft, which is stored on display 64 in the memory of microcomputer 32 sent to the processor of microcomputer. The processor determines the total flight time available by multiplying the total heat content by the heating value required per unit time for the flight conditions. The processor may transmit a signal representative of the total flight time through line 66 to a display 60.

As shown in FIG. 3, the method of the invention provides for the determination of the net heating value of fuel in an aircraft fuel tank by providing signals related to the density and temperature of the fuel, and determining the net heating value from those signals. The method also includes visibly displaying the net heating value, density and temperature of the fuel. Stored algorithms, such as equation I, may be used to determine the heating value of the fuel. Alternatively, the heating value of the fuel is determined using stored data. Length of time of flight and flight distance available from the fuel in fuel tank(s) and quantity of fuel required for an aircraft to make a specific flight are determined by using said net heating value.

FIG. 4 shows an aircraft 110 having a system for determining and displaying fuel heating value. The mobile storage tank 111 is connected by hose 111' to fuel tank 112'. The aircraft 110 includes fuel tanks 112, and 112', signal conditioner 114, and display 116. The signal conditioner 114 includes microprocessor, memory and analog to digital converter (A/D) as shown in FIG. 1 for signal conditioning 114. Density sensors 118 and 118' and temperature sensors 120 and 120' are supported by fuel tanks 112 and 112' respectively.

The signal conditioner 114 receives temperature and density signals through lines 122, 122', 124 and 124' respectively from temperature sensors 120 and 120' and density sensor 118 and 118' respectively. Signal conditioner 114 converts the density signal to a heating value signal. The display 116 received the heating value signal from signal conditioner 114 through line 130. The heating value signal is displayed by display 116. Capacitive probes 154 and 154' are connected by lines 156 and 156' respectively to signal conditioner 114.

Figure 5:
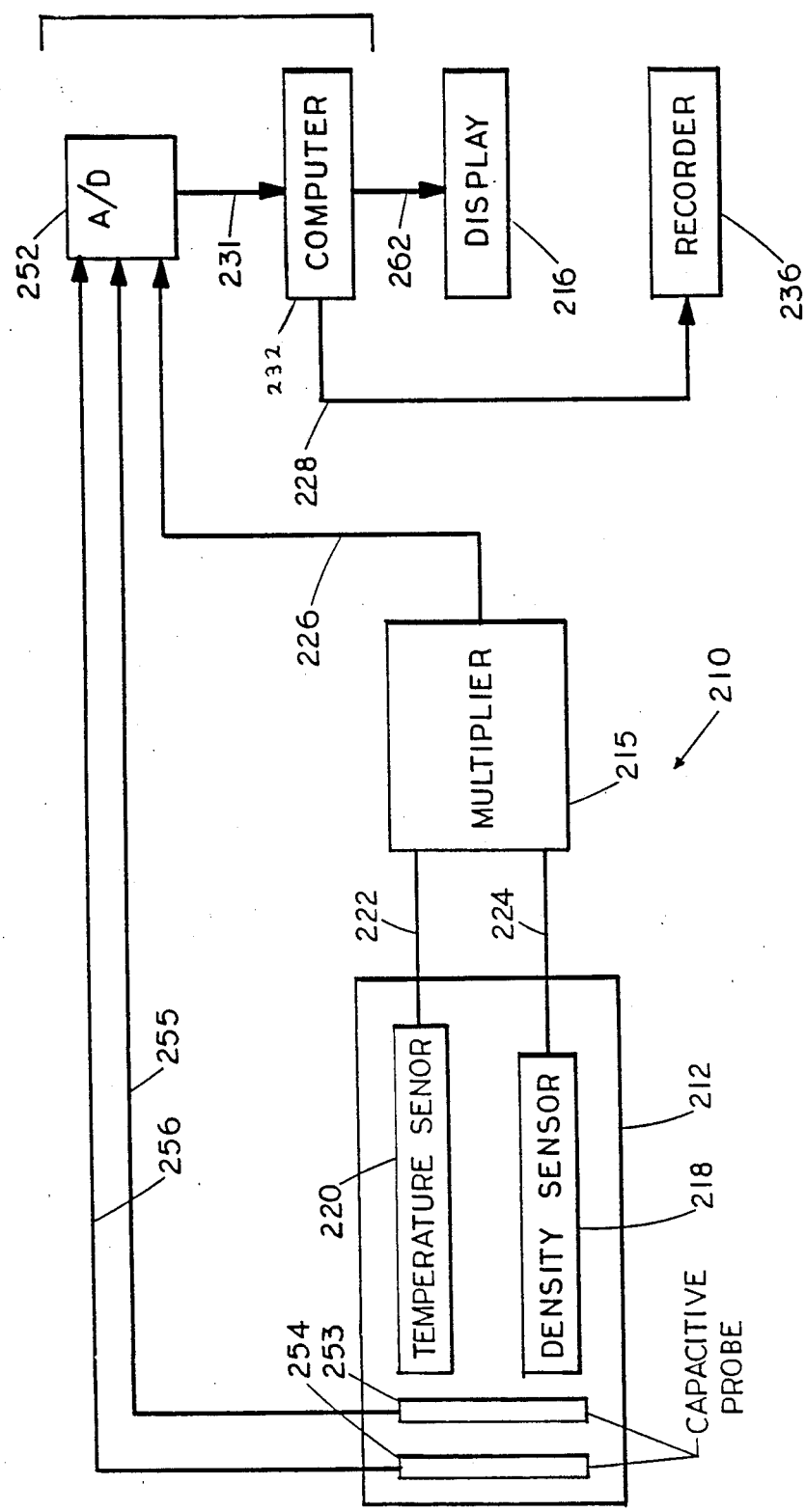
FIG. 5 shows a schematic representation of a system for determining and displaying net fuel heating value in accordance with the invention.

FIG. 5 shows a system for determining and displaying fuel heating value is shown generally at 210. The system 210 includes fuel container 212, multiplier 215 and display 216. The density sensor 218 and temperature sensor 220 are supported by fuel container 212.

The multiplier 215 receives temperature and density signals through lines 222 and 224 from temperature sensor 220 and density sensor 218 respectively. Multiplier 215 converts the density signal to an analog heating value signal, which is converted to a digital signal in analog to digital converter (A/D) 252. Capacitive probes 253 and 254 provide fuel quantity signals through lines 255 and 256 respectively to converter 252. Converter 252 is connected to computer 232 through line 231.

FIG. 3 shows the steps of the method in accordance with the present invention. Using sensors in a fuel tank, the temperature, density and quantity Q of fuel in the tank are measured. The quantity of fuel in the tank may be expressed in units of mass or volume. The sensor measurements are transmitted to the computer which then searches in memory to find the table for the temperature closest to the temperature measured. This table is then searched to locate the net heating value of the fuel in the tank which is stored with the density closest to the fuel density measured. Once located, the net heating value is stored separtely along with the density and quantity of fuel in the tank. The measurements of temperature, density and quantity of fuel in a fuel tank are repeated for each fuel tank on an aircraft or on a fuel transportation vehicle.

Having thus determined the net heating value of the fuel in the fuel tank, the quantity of fuel which is required for a specific flight is then determined. The specific flight for a time (t) and rate of fuel usage (R) by a specific aircraft is given by equation (II). The quantity of fuel may be expressed as a volume or a mass of fuel based on the net heating value per unit of volume or mass of the fuel determined as described herein above. The quantity of fuel required for the specific flight is then available to be displayed. The quantity of fuel required for the specific flight is loaded into the fuel tanks of the aircraft.

The flight time available from the quantity of fuel in each fuel tank or in all of the fuel tanks in an aircraft may be determined for the rate of fuel usage for a specific flight. The flight time (t) available from a quantity of fuel having a net heating value which has been measured as herein described above is given by equation (III).

$$t = (Q)/R \quad \text{(III)}$$

The flight time available from the quantity of fuel in one or more fuel tanks is then available to be displayed.

The net heating value for the fuel in one or more fuel tanks may be displayed in units of energy per unit mass, such as BTUs per pound or in units of energy per unit volume, such as BTUs per gallon. The display of net heating value for the fuel may be provided for each tank or for all tanks. The total heating value in units of energy, such as BTUs, for the quantity of fuel measured for each tank or for all tanks, may be displayed.

The foregoing describes the preferred embodiments of the invention. It will be understood by those of ordinary skill in the art that other embodiments and variants are within the spirit and scope of the invention as defined by the following claims.

What is claimed is:

1. An aircraft system for display of information relating to net heating value of liquid fuel comprising:
   an aircraft,
   a container,
   a display,
   a density sensor,
   a temperature sensor and a microprocessor means, said microprocessor means comprising a microprocessor;
   said container being supported by said aircraft and adapted to contain liquid fuel;
   said liquid fuel having a density, a temperature and a net heating value,
   said density sensor being adapted to sense said density of said liquid fuel and provide a density signal relating to said density;
   said temperature sensor being adapted to sense said temperature of a liquid fuel and provide a temperature signal relating to said temperature;
   said density sensor and said temperature sensor being supported within said container;
   said density sensor and said temperature sensor being positioned to be in contact with said liquid fuel;
   said density sensor and said temperature sensor being connected to said microprocessor means;
   said microprocessor means being adapted to provide a net heating value signal relating to said net heating value of said liquid fuel using said density and temperature signals;
   said display being connected to said microprocessor means, said microprocessor means being adapted to transmit said net heating value signal to said display;
   said display being adapted to receive said net heating value signal and to display information relating to said net heating value.

2. Method of providing information relating to net heating value of liquid fuel in an aircraft fuel tank comprising:
   a. providing an aircraft, a fuel tank, a density sensor, a temperature sensor, a microprocessor means and a display, said tank being supported by said aircraft, said microprocessor means comprising a microprocessor, said tank containing liquid fuel, said liquid fuel having a density, a temperature and a net heating value, said density and temperature sensors being in contact with said liquid fuel, said density and temperature sensors being connected to said microprocessor means, said microprocessor means being connected to said display,
   b. providing a signal related to said density of said fuel from said density sensor to said microprocessor means,
   c. providing a signal related to said temperature of said fuel from said temperature sensor to said microprocessor means,
   d. determining said net heating value of said fuel by said microprocessor means using said signal related to said temperature and said signal related to said density of said fuel,
   e. transmitting a net heating value signal relating to said net heating value of said fuel from said microprocessor means to said display, and
   f. displaying information relating to said net heating value.

3. The method of claim 2 wherein said determining of said net heating value includes using a algorithm stored in a memory connected to said microprocessor.

4. The method of claim 2 wherein data stored in a memory connected to said microprocessor is used by said microprocessor to determine said net heating value.

5. The method of claim 2 further comprising determining flight distance available for a specific aircraft from said fuel in said fuel tank.

6. The method of claim 2 further comprising determining length of time of flight available for a specific aircraft from said fuel in said fuel tank.

7. The method of claim 2 wherein said information displayed is a flight time available from said fuel for said airplane.

8. In a method of operating a jet aircraft on a specific flight, said jet aircraft supporting at least one fuel tank, and determining an amount of a selected liquid aircraft fuel having an actual heating value required to make said flight and to be loaded into said tank, the improvement comprising:

provided signal processing means, said signal processing means comprising a memory, said memory being adapted to store data relating to actual density and actual heating value for a plurality of liquid aircraft fuels, said signal processing means being adapted to use said data to determine an actual amount of said selected fuel required for said flight, determining the density and temperature of said fuel, determining the actual heating value of said fuel using the temperature and density of said fuel, and loading at least said actual amount of said selected liquid aircraft fuel required for said flight into said fuel tank, said actual amount of said selected liquid aircraft fuel required for said flight being less than an amount of liquid fuel having a lower heating value required for said flight.

9. The method of claim 8 wherein said signal processing means comprises a microprocessor.

10. The method of claim 8 wherein said actual heating value of said fuel is determined by
  a. providing at least a portion of said liquid fuel in an aircraft fuel tank,
  b. providing a signal related to the density of said fuel from a density sensor to a microprocessor,
  c. providing a signal related to the temperature of said fuel from a temperature sensor to said microprocessor,
  d. transmitting the actual heating value of said fuel from said microprocessor to a display.

11. The method of claim 9 wherein said microprocessor is connected to said display.

12. The method of claim 8 wherein said actual heating value of said fuel is determined in units of energy per unit mass.

13. The method of claim 8 wherein said amount loaded of said selected liquid aircraft fuel is essentially equal to said actual amount required for said flight.

* * * * *